(12) United States Patent
Livi et al.

(10) Patent No.: US 6,207,655 B1
(45) Date of Patent: Mar. 27, 2001

(54) BIS-PHOSPHONATE CONFUGATES WITH ALKYLATING MOIETIES HAVING ANTITUMOR ACTIVITY

(75) Inventors: Valeria Livi; Silvano Spinelli; Marco Conti; Simonetta D'Alo' ; Ernesto Menta, all of Monza (IT)

(73) Assignee: Novuspharma S.p.A., Monza (IT)

( * ) Notice: Subject to any disclaimer, the term of this patent is extended or adjusted under 35 U.S.C. 154(b) by 0 days.

(21) Appl. No.: 09/381,701

(22) PCT Filed: Mar. 24, 1998

(86) PCT No.: PCT/EP98/01707

§ 371 Date: Jan. 13, 2000

§ 102(e) Date: Jan. 13, 2000

(87) PCT Pub. No.: WO98/43987

PCT Pub. Date: Oct. 8, 1998

(30) Foreign Application Priority Data

Mar. 27, 1997 (IT) ................................................ MI97A0730

(51) Int. Cl.⁷ ........................ A61K 31/19; A61K 31/215; A61K 31/66; C07F 9/38

(52) U.S. Cl. ............................ 514/107; 514/102; 560/40; 562/13

(58) Field of Search ........................... 560/37, 40; 562/13; 514/114, 102, 107

(56) References Cited

U.S. PATENT DOCUMENTS

| | | | | |
|---|---|---|---|---|
| 4,608,368 | * | 8/1986 | Blum et al. | 514/107 |
| 5,300,671 | * | 4/1994 | Tognella et al. | 562/13 |
| 5,446,187 | * | 8/1995 | Tognella et al. | 562/13 |

FOREIGN PATENT DOCUMENTS

| | | |
|---|---|---|
| 0 170 896 | 7/1985 | (EP) . |
| 88/06158 | 8/1988 | (WO) . |
| 89/07453 | 8/1989 | (WO) . |
| 91/05791 | 5/1991 | (WO) . |
| 92/18512 | 10/1992 | (WO) . |
| 97/49711 | 12/1997 | (WO) . |

* cited by examiner

*Primary Examiner*—Jean F. Vollano
(74) *Attorney, Agent, or Firm*—Arent Fox Kintner Plotkin & Kahn, PLLC

(57) ABSTRACT

The present invention relates to conjugates of 3-carboxy-4,4'-dihydroxyphosphorylbutenoic acids with alkylating agents, derivatives are endowed with marked antitumor activity, especially against multiple myeloma. The present invention relates as well to a process for the preparation thereof and to pharmaceutical compositions containing them.

11 Claims, No Drawings

BIS-PHOSPHONATE CONFUGATES WITH ALKYLATING MOIETIES HAVING ANTITUMOR ACTIVITY

The present invention relates to conjugates of 3-carboxy-4,4'-dihydroxyphosphorylbutenoic acids with alkylating agents. Such derivatives are endowed with marked antitumor activity, especially against multiple myeloma. The present invention relates as well to a process for the preparation thereof and to pharmaceutical compositions containing them.

The skeletal system is the third more common site of metastases and more than 80% of the total number of patients dead for cancer show bone tumors at the autopsy. Bone metastases account for a significant proportion of cancer-related morbidity, causing derangement in calcium metabolism and bone marrow involvement and are responsible for the consequences of most concern to patients with cancer, such as pain, pathologic fractures, compression of the spinal cord and hypercalcemia (Drew et al., Osseous complication of malignancy, Lokich, J. J. ed. Clinical cancer medicine: treatment tactics Boston: G. K. Hall Medical Publisher, 1980, 97–112).

One of the main problems to overcome in connection with the conjugates between osteotropic carriers and cytotoxic agents is the selective release of the cytotoxic agent to the bone. The molecules characterized by an amide bond may result too stable to the hydrolysis by the lysosomial enzymes. To obtain the selective release of the cytotoxin to the bone acid-labile bonds may be used. It is known that the osteoclasts generate an acidic microenvironment inside the bone resorption area. The low pH value is necessary in order to remove the mineral component (the solubility of calcium hydroxyapatite depends on the pH: the complex is almost totally insoluble at physiologic pH, while it dissolves at a 50 mM concentration of $Ca^{++}$ ions at about pH=3.5) and to remove the organic matrix by means of the lysosomial cathespins secreted by the same cells. The lower pH measured "in vivo" was 4.7, but the average pH was 6.01 (Silver A, et al., Experimental Cell Res., 175, 266–76 (1988)). The bis-phosphonates act at the osteoclast/bone interface and localize preferentially at the bone resorption sites. When the osteoclasts begin the resorption process, the bis-phosphonate, as a result of the acidification, is released from the bone surface toward the resorption area (Rodan G. A., Bone, 1, S1–S6, 1992). In this way an acid labile conjugate may be hydrolyzed and the cytotoxin may be selectively released inside the resorption area.

Moreover it is known that the tumor cells are able to stimulate the osteoclast's resorption activity, which causes a continuous acidification of the resorption area. Pro-drugs of daunomycin are known which contain the cis-aconitic acid as a spacer between the cytotoxin and the protein carrier (Shen W. C. et al., Biochem. and Biophysical Res. Comm., 102, 1048–54, 1981). It is reported that such molecules are stable in plasma at pH 7.4, while are hydrolized in the lysosomial compartment at pH<5.5. Such an effect is accomplished by means of the ability of the free carboxyl group of the aconitic acid to react on the amide bond formed by the other carboxyl group with the cytotoxin, by catalysing its hydrolysis.

Gem-diphosphonic acids and salts thereof are known and employed in the therapy of the osteoporosis and in the treatment of bone resorption (see EP 096 931, EP 252 504, BE 896.453, BE'903.519, DE 3.016.289, DE 3.540.150, DE 2.534.391, DE 3.512.536). However none of the above compounds is described to possess antitumor activity.

DE 3.425.812 (Blum et al.) describes derivatives of 1,1-diphosphonic acids, characterized by a bis[(haloalkyl) amino]phenyl residue, as agents useful in the treatment of bone tumors.

In WO 88/06158 are moreover described diphosphonic analogues of methotrexate as agents useful in the treatment of bone tumors.

In WO 92/18512 are described conjugates of melphalan with gem-diphosphonic acids, in which the two reactive groups are linked by amino acids.

WO91/05791 (Feb. 5, 1991) discloses gem-diphosphonic acid derivatives of melphalan wherein the alkylating moiety is attached to the carbon atom to which the phosphoric groups are bound through a spector comprising an amide bond.

Our research was addressed toward the modification of the structure of aconitic acid in order to confer affinity for the bone tissue and toward the coupling of the so obtained carriers with alkylating residues.

We have found that by coupling a diphospho-aconitic carrier with a cytotoxic agent, compounds exploiting a marked affinity for the bone tissue are obtained. Such compounds are endowed with a high antitumor activity, in particular against multiple myeloma.

Human multiple myeloma is a circulating tumor which hits the plasma cells. One of its target organs is bone marrow, from which the tumor invades the surrounding bone tissue and causes serious pathological consequences to the patient, such as pain and fractures. Although melphalan exploits activity against the multiple myeloma, it is not able to cure the secondary bone tumor. It is therefore evident that to have found compounds able to cure this latter too is a noteworthy clinical advantage. It should be noticed that any bis-phosphonate in the state of the art has been shown active against the multiple myeloma.

The present invention relates to compounds of the general formula (I):

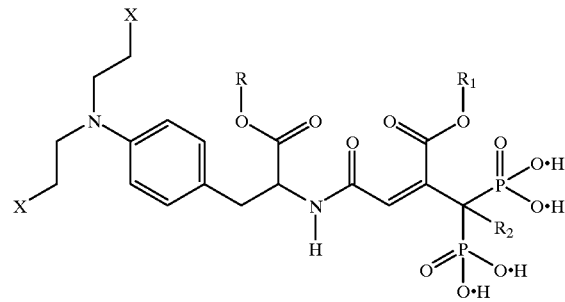

(I)

wherein:
R, $R_1$ and $R_2$ are independently selected in the group consisting of hydrogen, methyl, ethyl, propyl, butyl, which can be linear or branched, with the proviso that $R_1$ cannot be tert-butyl;
X is chlorine, bromine or iodine;
enantiomers, racemates, diastereoisomers and mixtures thereof, as well as salts thereof with pharmaceutically acceptable bases.

The C=C double bond in the aconitic residue as shown in formula (I) has a purely indicative stereochemistry, being included in the present invention both cis and trans stereoisomers, wherein "cis" or "trans" relates to the relative position of the carboxyl and carboxamide groups.

Preferred compounds of formula (I) are those in which X is chlorine.

Other preferred compounds of formula (I) are those in which R, $R_1$ and $R_2$ are hydrogen.

Particularly preferred compounds of formula (I) are those in which the C=C double bond in the aconitic residue has a cis stereochemistry.

The compounds of formula (I) can be prepared by means of a process which comprises the following synthesis steps (where not expressly specified, the C=C double bonds stereochemistry is purely indicative):

(a) reaction of a compound of formula (II):

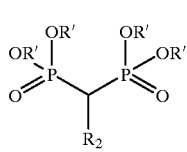
(II)

in which the R' groups are linear $(C_1-C_4)$alkyl groups, with a compound of formula (III):

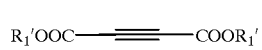
(III)

in which the $R_1'$ groups are linear $(C_1-C_4)$alkyl groups, in the presence of a base, to give an intermediate of formula (IV):

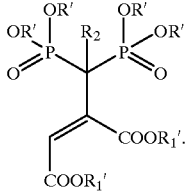
(IV)

The compounds of formula (IV) are known compounds [J. Org. Chem., 45(13), 2698–2703 (1980)].

(b) hydrolysis of the $R_1'$ ester groups, preferably in alkaline conditions, to give the intermediates of formula (V):

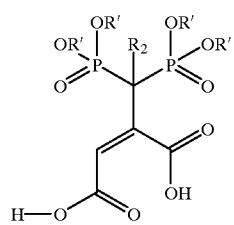
(V)

optionally in the form of salts with the used base;

(c) cyclization reaction of intermediates of formula (V) in the presence of a dehydrating agent to give the anhydrides of formula (VI):

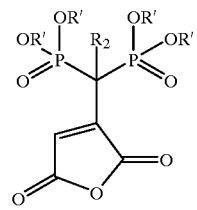
(VI)

(d) condensation reaction of an anhydride of formula (VI) with a compound of formula (VII):

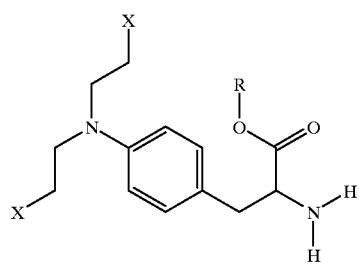
(VII)

to give the compounds of formula (VIII):

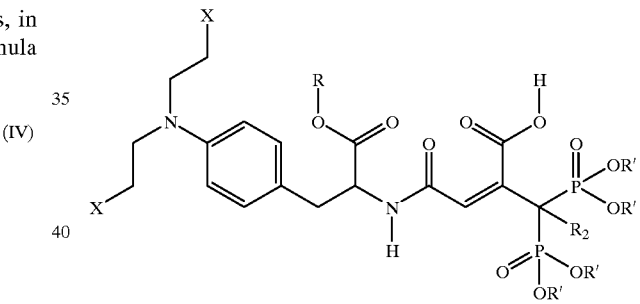
(VIII)

(e) optional esterification of the free carboxyl group of a compound of formula (VIII) to give the compounds of formula (IX):

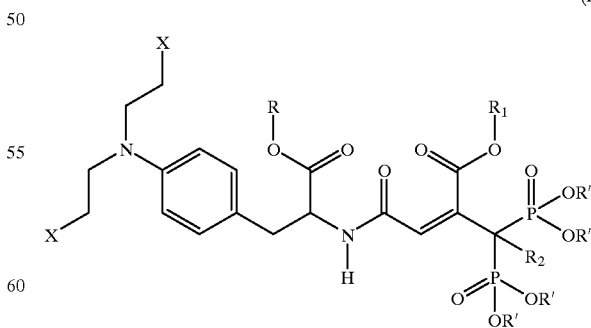
(IX)

Compounds of formula (IX) in which R is hydrogen may be obtained by esterification of the free carboxyl group of a compound of formula (VIII) in which R is tert-butyl and subsequent hydrolysis of the tert-butyl group;

(f) hydrolysis of the phosphonic esters of a compound of formula (VIII) or (IX) to give the wanted compounds of formula (I).

The condensation reaction of step (a) is preferably performed in inert solvents such as for example benzene or toluene, and in the presence of a strong base, such as for example a hydride of an alkali or alkaline-earth metal, at temperatures ranging from −10° C. and the boiling point of the solvent, preferably between 0° C. and room temperature. A slight excess of intermediate of formula (III) is preferred.

The hydrolysis reaction of step (b) is preferably performed in the presence of an inorganic base, such as for example a hydroxide of an alkaline or alkaline-earth metal, in water, an alcohol or mixtures thereof. The temperature can vary from 0° C. to 70° C., preferably at room temperature.

The cyclization reaction of step (c) is preferably performed in the presence of a dehydrating agent such as for example a carbodiimide or an anhydride, in an inert solvent such as for example an ether (dimethoxyethane, tetrahydrofuran) and at temperatures ranging from −10° C. to 50° C., preferably between 0° C. and room temperature. A preferred dehydrating agent is trifluoroacetic anhydride.

The condensation reaction of step (d) is preferably performed using until 50% excess of intermediate of formula (VI) and in the presence of a base, such as for example an organic base (trialkylamine) in large excess (5–15 equivalents), working in a solvent, preferably a polar solvent such as acetonitrile, and at temperatures ranging from 0° C. to the boiling point of the solvent, more preferably at room temperature.

The esterification reaction of step (e) is preferably performed in the presence of an activating agent for the carboxyl group, such as for example an anhydride or a carbodiimide, in an inert solvent. The hydrolysis of the tert-butyl group is preferably performed in acidic conditions, such as for example by means of trifluoroacetic acid.

The hydrolysis reaction of the phosphonic esters of step (f) is preferably performed by means of trimethylsilyl iodide in an inert solvent such as for example toluene and at temperatures ranging from 0° C. to 50° C., more preferably at room temperature.

The compounds of formula (II) can be obtained from the corresponding compounds of formula (II'):

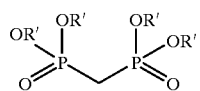

(II')

by reaction with an alkyl halide of formula R$_2$—Alg, in which Alg is selected from the group consisting of chlorine, bromine and iodine, in the presence of a strong base such as for example an alkaline metal or a hydride thereof, according to the methods described for example in Phosphorus, Sulphur and Silicon, 1994 (88), pp. 1–13, J.C.S., 1953, pp. 1500–1501 e Heterocycles, 1990, pp. 855–862.

The compounds of formula (III) are commercial products.

The compounds of formula (VII) are compounds well known to the expert in the art who works in the field of the antitumor agents. Melphalan (X=chlorine and R=hydrogen) is a clinically used antitumor drug.

The compounds of the invention have been tested "in vivo" against the murine breast carcinoma Walker 256/B implanted intratibia (it). After inoculation into the bone marrow cavity of the tibia, this tumor grows inside the bone causing osteolytic lesions, paraneoplastic hypercalcaemia and by invading the surrounding tissues it forms a measurable tumor mass. It is therefore possible to determine both the antitumor activity on the extraosseous tumor and the anti-osteolytic effect (Cancer, 72(1), 91 (1993)).

The Walker 256/B tumor was provided by NCI Frederick Cancer Facility and was maintained in male rats CD1 by means of subcutaneous transplantation of tumor fragments of about 1 cm diameter every 10 days.

To perform the experiment, each rat was injected it with 2.5×10$^6$ tumor cells; all the animals were anesthetized with a mixture of 10 mg/kg of Ketalar (Park-Davis) and 5 mg/kg of Rompun (Bayer). After implantation inside the tibia, the tumor grows causing osteolytic lesions associated with an increased activity of the osteoclasts. To obtain an injectable cell suspension, the tumor fragments were decomposed by means of enzymatic digestion with type IV collagenases (Sigma) at a concentration of 400 U/ml for 20 minutes at 37° C.

The compounds of the invention have been administered i.v. at days 1, 4 and 7 after the tumor transplantation. The extraosseous tumor mass has been measured at day 14 after tumor transplantation. The antitumor activity was determined as TWI% (tumor weight inhibition %) calculated according to the following formula:

$$TWI\% = (100 - TW\ mean_{treated\ animals}/TW\ mean_{controls}) \times 100$$

wherein the TW for each animal is given by the formula:

$$TW = \frac{1}{2}(ab)^2$$

in which a and b are respectively the maximum and minimum diameter of the tumor mass, expressed in mm.

The compounds of the invention resulted in addition active in an experimental model of human multiple myeloma on the lab animal.

The experiment is performed by inoculating intravenously (i.v.) the human multiple myeloma HS-Sultan cells in SCID rats (immunodeficient rats) at day 0, followed by treatment i.v. with a compound of the invention at days 15, 18 and 21.

The activity of the compounds of the invention was evaluated in relationship with the following parameters:

Mean Survival Time (MST) in comparison with the not treated rats (which have a mean survival time of 30 days after tumor inoculation);

evaluation of histological parameters (bone marrow invasion and degree of osteolytic lesions).

Table I summarizes the data for one representative compound of the invention in comparison with melphalan and with the prior art compound (WO 92/18512) of formula (A):

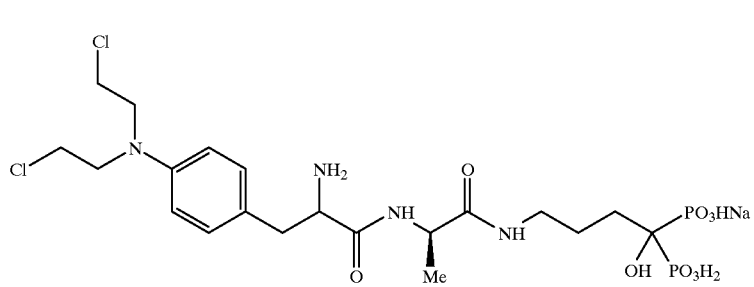

(A)

TABLE I

Antitumor activity against murine breast carcinoma Walker 256/B and human myeloma HS-Sultan

| Compound | Walker 256/B it/iv 1, 4, 7 | | | BS-Sultan iv/iv + 15, 18, 21 | | |
|---|---|---|---|---|---|---|
| | dose (mg/kg) | TWI % | Tox | dose (mg/kg) | TMS[1] | Tox |
| compound (B) | 20 | 89 | 0/8 | 60 | 70 | 1/6 |
| compound (A) | 10 | 66 | 1/8 | 15 | 55 | 1/5 |
| melphalan | 2.8 | 71 | 11/144 | 6 | 59 | 1/5 |

[1]MST = Mean Survival Time in days from the tumor inoculation (controls: MST 33–37).

The histopathological examination on some representative target organs, in the human multiple myeloma model, performed after 38 days from the treatment, showed the following tumor infiltration scores (−absence of infiltration; +slight infiltration; ++middle to high infiltration);

| | melfalan (6 mg/kg) | (A) (15 mg/kg) | (B) (oO mg/kg) |
|---|---|---|---|
| Sternum | + | + | − |
| Backbone | + | + | − |
| Backbone (soft tissues) | − | + | − |
| Hind limbs | + | ++ | − |
| Hind limbs (soft tissues) | − | + | − |
| Kidneys | − | − | + |

The data clearly show that the compound of the invention (compound (B)) has a selective inhibitory effect on the tumor infiltration which cannot be seen neither with melphalan nor with the prior art conjugate between melphalan and a gem-diphosphonic acid (compound (A)).

The compounds of the invention are endowed with a low acute toxicity and are well tolerated by the animal.

The high water solubility of the compound of the invention allows to prepare parenteral and oral pharmaceutical forms.

The compounds of formula (I), when administered to humans and animals bearing tumors susceptible of treatment with alkylating agents, in doses ranging from 1 mg to 1200 mg for square meter of body area, are able to induce regression of said tumor forms and to improve the bone tissue repair, avoiding in this way the pathological consequences caused by the bone lesions.

The effective dosage of the compounds of the invention can be determined by an expert clinician with known and conventional methods.

The correlation between dosages used for animals of various species and those for humans (as mg/m$^2$ of body area) is described in Freirich, E. J. et al., Cancer Chemother. Rep., 50, n. 4, 219–244, May 1966.

The tumors which can be treated by the compounds of the present invention are those tumors susceptible to the therapy with alkylating agents.

In particular, the multiple myeloma, osteosarcoma, bone metastases, breast, ovary and testicular carcinomas can be advantageously treated.

The pharmaceutical compositions containing the compounds of formula (I) are encompassed in the scope of the invention. Such pharmaceutical compositions may contain whatever amount of compounds of formula (I) able to exert an antitumor activity on the mammals against the tumors susceptible to the therapy with alkylating agents.

The pharmaceutical compositions may contain, in addition to at least one compound of formula (I), pharmaceutically compatible excipients, so that to allow the administration by every route, such as oral, parenteral, intravenous, intradermal, subcutaneous or topic route, in liquid or solid form.

An administration route of the compounds of formula (I) is the oral route. Oral compositions will generally include an inert diluent or an edible carrier. They may be included in gel capsules or compressed into tablets. Other oral administration forms are capsules, pills, elixirs, suspensions or syrups.

The tablets, pills, capsules and similar compositions may contain the following ingredients (in addition to the active principle): a binder such as microcrystalline cellulose, tragacanth or gelatin; an excipient such as starch or lactose; a disintegrating agent such as alginic acid, primogel, maize starch and the like; a lubricant such as magnesium stearate; a fluidifier such as colloidal silicon dioxide; a sweetening agent such as sucrose or saccharine or a flavouring agent such as mint flavour, methyl salicylate or orange flavour. When the composition selected is in form of capsules, it can contain in addition a liquid carrier such as a fat oil. Other compositions can contain various material which change the physical form thereof, for example coating agents (for tablets and pills) such as sugar or shellac. The material used in the preparation of the compositions should be pharmaceutically pure and non toxic at the dosages employed.

For the preparation of pharmaceutical compositions for the parenteral administration, the active ingredient can be included in solutions or suspensions, which can comprise in addition the following components: a sterile diluent such as water for injections, saline solution, oils, polyethylene glycols, glycerin, propylene glycol or other synthetic solvents; antibacterial agents such as benzyl alcohol; antioxidants such as ascorbic acid or sodium bisulfite; chelating agents such as ethylenediamino tetraacetic acid; buffers such as acetates, citrates or phosphates and agents for adjusting the tonicity of the solution, such as sodium chloride or dextrose. The parenteral preparation can be included in ampoules, mono-dose syringes, glass or plastic vials.

The invention is further illustrated by the following examples.

EXAMPLE 1

Synthesis of 2-[bis(diethoxyphosphoryl)methyl] maleic Acid Dimethyl Ester

In a suspension of 1.33 g of sodium hydride (60% in oil) in 120 ml of toluene are added dropwise 10 g of bis(diethoxyphosphoryl)methane dissolved in 20 ml of toluene. The reaction mixture is kept at room temperature under stirring for 1 hour, then it is cooled to 0° C. and added dropwise with a solution of dimethyl acetylenedicarboxylate (5.17 g) in 20 ml of toluene. After 1 hour under stirring the reaction mixture is added with ethyl acetate until dissolution of the formed gummy solid occurs and it is washed firstly with 1 N hydrochloric acid (30 ml) then with water (2×30 ml). The organic phase is dried over sodium sulfate and the solvent is evaporated under reduced pressure, to give a residue (12.9 g) which, after purification by silica gel chromatography (300 g; eluent:petroleum ether/isopropanol 7:3) furnishes 9.6 g of pure product.

$^1$H NMR in CDCl$_3$: 1.35 ppm (m, 12H); 3.77 ppm (s, 3H); 3.80 ppm (s, 3H); 3.85 ppm (t, 1H); 4.20 ppm (m, 8H); 6.9 ppm (t, 1H).

EXAMPLE 2

Synthesis of 2-[bis(diethoxyphosphoryl)methyl] maleic Acid

A solution of 12.7 g of 2-[bis(diethoxyphosphoryl)methyl]maleic acid dimethyl ester in 76.8 ml of 1 N sodium hydroxide is kept under stirring for 96 hours, then the reaction mixture is washed twice with ethyl ether and is brought to pH 8.5 with 37% hydrochloric acid. The mixture is then concentrated to dryness and redissolved in 50 ml of methanol. After filtration of the formed sodium chloride, the solvent is evaporated under reduced pressure. The residue is treated with 125 ml of acetone, to give, after filtration, 11.5 g of the product as disodium salt.

$^1$H NMR in D$_2$O: 1.30 ppm (m, 12H); 4.17 ppm (m, 8H); 6.10 ppm (t, 1H); 6.56 ppm (t, 1H); 6.67 ppm (t, 1H).

EXAMPLE 3

Synthesis of 2-[bis(diethoxyphosphoryl)methyl] maleic Anhydride

A solution of 2.5 g of 2-[bis(diethoxyphosphoryl)methyl] maleic acid disodium salt in 50 ml of acetone is added with 2.13 g of para-toluenesulphonic acid. After 8 minutes under stirring, the formed sodium para-toluenesulphonate is separated by filtration and solvent is evaporated under reduced pressure. The residue is redissolved in 7.5 ml of anhydrous tetrahydrofuran and cooled to 0° C., then it is added dropwise with 3.8 ml of trifluoroacetic anhydride. The reaction mixture is refluxed for 30 minutes, then it is cooled to room temperature and concentrated to dryness. The residue is treated with ethyl ether, filtered and concentrated to dryness. This work up is repeated twice with toluene. 2.7 g of the product are obtained.

$^1$H NMR in CDCl$_3$: 1.35 ppm (m, 12H); 3.95 ppm (t, 1H); 4.25 ppm (m, 8H); 7.12 ppm (t, 1H).

EXAMPLE 4

Synthesis of (2'E)-N-(3'-carboxy-4,4'-diethoxyphorphoryl-2'-butenoyl)-4-[bis(2-chloroethyl)amino]-L-phenylalanine In a solution of 2.9 g of melphalan in 290 ml of acetonitrile, 29 ml of water and 13 ml of triethylamine, are added dropwise 6 g of 2-[bis(diethoxyphosphoryl)methyl] maleic anhydride dissolved in 60 ml of acetonitrile. The reaction mixture is kept under stirring for 3 hours, then the solvent is evaporated under reduced pressure. The residue is dissolved in ethyl acetate and washed with 1 N hydrochloric acid (100 ml) and then with water (2×25 ml). The organic phase is dried over sodium sulfate and the solvent is evaporated under reduced pressure to give 7 g of residue which is purified by silica gel chromatography (350 g; eluent: from ethyl acetate to ethyl acetate/methanol 9:1) to give 3.48 g of the product.

$^1$H NMR in CDCl$_3$: 1.15–1.45 ppm (m, 12H); 2.75 ppm (dd, 1H); 3.1 ppm (dd, 1H); 3.55 ppm (m, 8H); 4.0–4.4 ppm (m, 8H); 4.82 ppm (m, 1H); 4.87 ppm (t, 1H); 6.55 ppm (d, 2H); 7.02 ppm (d, 2H); 7.55 ppm (t, 1H); 8.85 ppm (d, 1H).

EXAMPLE 5

Synthesis of (2'E)-N-(3'-carboxy-4,4'-dihydroxyphosphoryl-2'-butenoyl)-4-[bis(2-chloroethyl)amino]-L-phenylalanine Tetrasodium Salt A solution of (2'E)-N-(3'-carboxy-4,4'-dihydroxyphosphoryl-2'-butenoyl)-4-[bis(2-chloroethyl)

amino]-L-phenylalanine (3.23 g) in 177 ml of toluene, kept at 0° C. under stirring, is added dropwise with 4.6 ml of trimethylsilyl iodid. The temperature is brought to room temperature and the reaction mixture is kept under stirring for 3 hours, then it is poured into 640 ml of methanol containing 2.68 g of sodium acetate. The solution is brought from pH 6.5 to pH about 7 with 1 N sodium hydroxide, then 64 ml of water are added and the pH is again adjusted to pH 7.3. After 15 minutes under stirring, the mixture is filtered and the formed solid is washed with a few methanol. The solid is dried in an oven under vacuum overnight to give 2.43 g of the product.

$^{1}$H NMR in $D_2O$: 3 ppm (m, 2H); 3.25 ppm (t, 1H); 3.75 ppm (s, 8H); 4.45 ppm (t, 1H); 6.35 ppm (t, 1H); 6.85 ppm (d, 2H); 7.25 ppm (d, 2H).

EXAMPLE 6

Following the methods described in examples 1–5 the following gem-diphosphonic acids are prepared:

N-(3'-carboxy-4,4'-dihydroxyphosphoryl-4'-methyl-2'-butenoyl)-4-[bis(2-chloroethyl)amino]-L-phenylalanine tetrasodium salt;

N-(3'-carboxy-4,4'-dihydroxyphosphoryl-2'-butenoyl)-4-[bis(2-chloroethyl)amino]-L-phenylalanine methyl ester, tetrasodium salt;

N-(3'-carboxy-4,4'-dihydroxyphosphoryl-2'-butenoyl)-4-[bis(2-chloroethyl)amino]-L-phenylalanine ethyl ester, tetrasodium salt;

N-(3'-carboxy-4,4'-dihydroxyphosphoryl-4'-ethyl-2'-butenoyl)-4-[bis(2-chloroethyl)amino]-L-phenylalanine tetrasodium salt;

N-(3'-carboxy-4,4'-dihydroxyphosphoryl-4'-butyl-2'-butenoyl)-4-[bis(2-choroetyl)amino]-L-phenylalanine ethyl ester, tetrasodium salt.

What is claimed is:

1. A compound of the general formula (I):

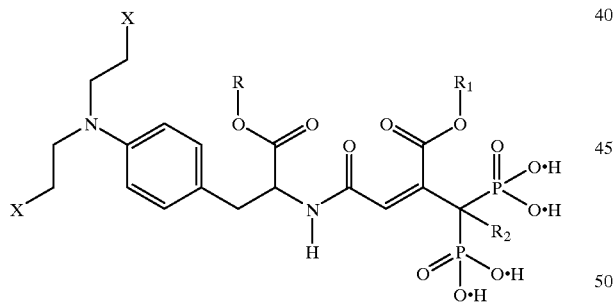

wherein:
R, $R_1$ and $R_2$ are independently selected from the group consisting of hydrogen, methyl, ethyl, propyl, butyl, which can be linear or branched, with the proviso that R1 cannot be tert-butyl;
X is chlorine, bromine or iodine; enantiomers, racemates, diastereoisomers and mixtures thereof, as well as salts thereof with pharmaceutically acceptable bases.

2. A compound according to claim 1, in which X is chlorine.

3. A compound according to claim 1, in which R, $R_1$ and $R_2$ are hydrogen.

4. A compound according to claim 1, in which the stereochemistry of the carboxyl and carboxyamide groups on the C=C double bond is cis.

5. Compound according to claim 1, wherein said compound is:
(2'E)-N-(3'carboxy-4,4'-bis(dihydroxyphosphoryl-2'-butenoyl)-4-[bis(2-chloroethyl)amino]-L-phenylalanine.

6. Process for the preparation of a compound of claim 1; which comprises the following steps:
(a) reacting a compound of formula (II):

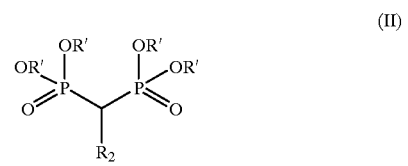

in which the R' groups are linear ($C_1$–$C_4$)alkyl groups with a compound of formula (III):

in which the $R_1$ groups are linear ($C_1$–$C_4$)alkyl groups, in the presence of a base, to give an intermediate of formula (IV):

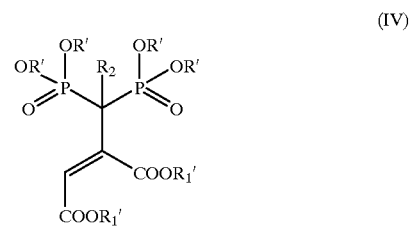

(b) hydrolyzing of the $R_1'$ ester groups to give the intermediates of formula (V):

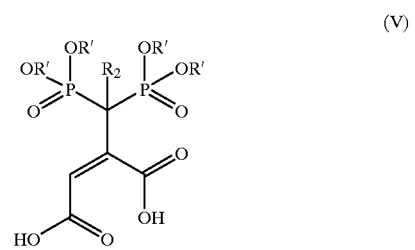

optionally in the form of salts with the used base;
(c) cyclization reacting of intermediates of formula (V) producing the anhydrides of formula (VI):

(VI)

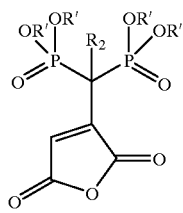

(d) condensing an anhydride of formula (VI) with a compound of formula (VII):

(VII)

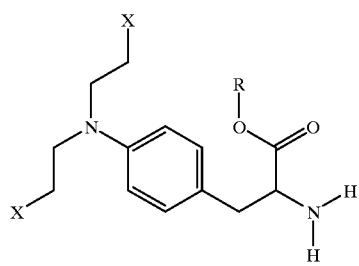

to give the compounds of formula (VII):

(VIII)

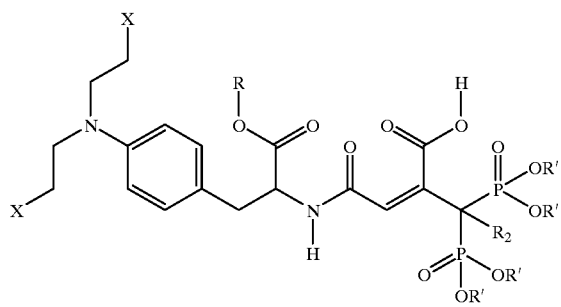

(e) optionally esterfying of the free carboxyl group of a compound of formula (VIII) to give the compounds of formula (IX):

(IX)

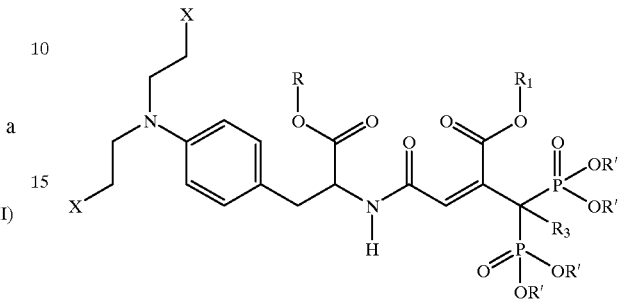

(f) hydrolyzing the phosphonic esters of a compound of formula (VIII) or IX) to give the wanted compounds of formula (I).

7. Process according to claim 6 for the preparation of the compounds of claim 1 with R=hydrogen, in which the free carboxyl group of a compound of formula (VIII) with R=tert-butyl is esterified, followed by removal of the tert-butyl group.

8. Pharmaceutical formulation containing pharmaceutically effective amounts of one or more compounds according to claim 1 in admixture with excipients or additives.

9. A medicament comprising a compound according to claim 1.

10. The medicament of claim 9 wherein said medicament is an antitumor agent.

11. The medicament of claim 10 wherein said antitumor agent is an anti multiple myeloma tumor agent.

* * * * *